United States Patent [19]

Cortes

[11] Patent Number: 4,946,993

[45] Date of Patent: Aug. 7, 1990

[54] 2-AZABICYCLO[2.2.1.]HEPT-5-ENE-2-ACETIC ACID, DERIVATIVES THEREOF AND RELATED COMPOUNDS, PROCESS FOR THE PREPARATION OF SAID COMPOUNDS, AND THE USE OF SAID COMPOUNDS FOR THE MANUFACTURE OF N-PHOSPHONOMETHYLGLYCINE

[75] Inventor: David A. Cortes, Fairless Hills, Pa.

[73] Assignee: American Cyanamid Company, Stamford, Conn.

[21] Appl. No.: 276,186

[22] Filed: Nov. 23, 1988

[51] Int. Cl.$^5$ .............................................. C07F 9/38
[52] U.S. Cl. ...................................... 562/17; 548/452
[58] Field of Search ................... 260/502.5 F; 562/17

[56] References Cited

U.S. PATENT DOCUMENTS

| | | | |
|---|---|---|---|
| 4,486,359 | 12/1984 | Brendel née Hajnóczki et al. | 260/502.5 F |
| 4,657,705 | 4/1987 | Miller et al. | 260/502.5 F |
| 4,775,498 | 10/1988 | Gentilcore | 260/502.5 F |

*Primary Examiner*—J. E. Evans
*Attorney, Agent, or Firm*—Alice C. Brennan

[57] ABSTRACT

The present invention describes a novel compound, 2-azabicyclo[2.2.1]hept-5-ene-2-acetic acid, its preparation and the preparation of related compounds and the use of said compounds as intermediates for the preparation of N-phosphonomethylglycine.

5 Claims, No Drawings

2-AZABICYCLO[2.2.1.]HEPT-5-ENE-2-ACETIC ACID, DERIVATIVES THEREOF AND RELATED COMPOUNDS, PROCESS FOR THE PREPARATION OF SAID COMPOUNDS, AND THE USE OF SAID COMPOUNDS FOR THE MANUFACTURE OF N-PHOSPHONOMETHYLGLYCINE

BACKGROUND OF THE INVENTION

The invention herein described relates to a new compound, 2-azabicyclo[2.2.1]hept-5-ene-2-acetic acid, the preparation of said new compound and its use as an intermediate in the process for the manufacture of N-phosphonomethylglycine, a known herbicide and plant growth regulator.

Methyl-2-azabicyclo[2.2.1]hept-5-ene-2-acetate (azanorbornene methyl ester) was described in the literature by Paul A. Grieco in J. Am. Chem. Soc., 1987, 109, pp 5859–5861 and J. Org. Chem. 1987, 52, pp 5746–5749. However, 2-azabicyclo[2.2.1]-hept-5-ene-2-acetic acid, the compound and its formation by an Aza Diels-Alder reaction in glacial acetic acid has not been reported in the literature.

N-Phosphonomethylglycine, the compound and its use as an important herbicidal agent is described in U.S. Pat. No. 3,799,758. N-phosphonomethylglycine and derivatives thereof are effective herbicides at low rates of application when applied postemergence and are biodegradable into harmless residues within a relatively short period of time after their application.

A number of processes for the preparation of N-phosphonomethylglycine have been described in a series of patents such as U.S. Pat. Nos. 4,053,505, 4,237,065, 4,415,503, and 4,428,888 among others. Many of these processes use glycinate esters or phosphinate esters, or both, necessitating additional materials and additional reaction steps for their formation.

There is an ongoing search in the art for better methods of preparation of this agronomically important compound. Surprisingly, it has been discovered that 2-azabicyclo[2.2.1]hept-5-ene-2-acetic acid (N-carboxymethylazanorbornene), derivatives thereof and related compounds can be used as key intermediates in a new and useful process to prepare N-phosphonomethylglycine. It is an object of the present invention to describe a novel compound and its preparation and to provide a new and useful method to prepare N-phosphonomethylglycine. This novel intermediate allows the preparation of N-phosphonomethylglycine from glycine and PCl₃ without the use of esters.

SUMMARY OF THE INVENTION

It has now been found that N-substituted azanorbornenes of formula I, wherein Y is COOR, CON(R₁)₂ or CN and R and R₁ are each independently hydrogen or C₁–C₄ alkyl, are useful intermediates for the production of N-phosphonomethylglycine.

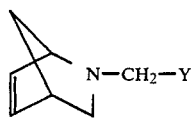

I

Compounds of formula I as hereinabove described may be formed by reacting aminomethyl compounds of formula II, or their protonated salts, wherein Y is as described above for formula I, with from about 0.90 to 10.0 molar equivalents of formaldehyde and from about 1.0 to 10.0 equivalents of cyclopentadiene in the presence of a solvent, as shown in Flow Diagram I.

FLOW DIAGRAM I

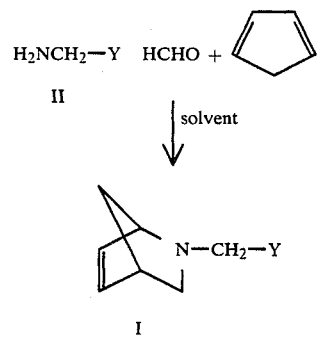

When Y is CON(R₁)₂ or CN, the presence of an acid is required. When Y is COOH, no additional acid is needed.

Dienes other than cyclopentadiene such as substituted cyclopentadienes, unsubstituted or substituted cyclohexadienes, and butadienes or substituted butadienes such as isoprene may also be employed in the reaction sequence illustrated in Flow Diagram I to give the corresponding azanorbornenes, azabicyclo[2.2.2]-octenes, and azacyclohexenes respectively.

The N-substituted azacycloalkene or azabicycloalkene intermediates so obtained, such as the N-substituted azanorbornene intermediates of formula I, preferably wherein Y is COOH, may be reacted with a dialkylphosphite or a phosphorous trihalide, preferably phosphorous trichloride, in the presence of a solvent, preferably a lower alkyl carboxylic acid, preferably acetic acid, followed by hydrolysis in the presence of aqueous acid or base, preferably acid, to produce N-phosphonomethylglycine as illustrated in Flow Diagram II, wherein Y is as described hereinabove, R₂ is C₁–C₄ alkyl, and X is Cl or Br.

FLOW DIAGRAM II

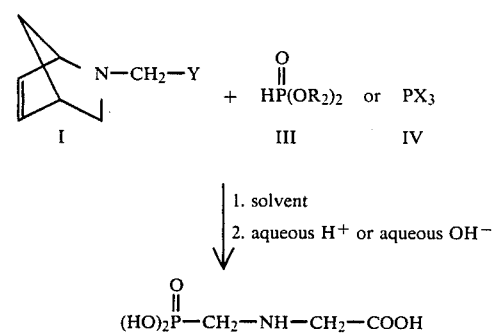

DESCRIPTION OF THE INVENTION

The invention relates to a novel compound, 2-azabicyclo[2.2.1]hept-5-ene-2-acetic acid, derivatives thereof and related compounds, the preparation of said compounds and a novel method to prepare N-phosphonomethylglycine via the N-substituted azabicycloalkene or N-substituted azacycloalkene intermediates such as the N-substituted azanorbornene intermediate of formula I

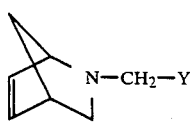

wherein Y is COOR, CON(R$_1$)$_2$, OR CN; and R and R$_1$ are each independently hydrogen or C$_1$-C$_4$ alkyl.

Compounds of formula I may be prepared by reacting aminomethyl compounds of formula II or the protonated salts thereof, wherein Y is as described for formula I, with from about 0.9 to 10.0 molar equivalents of formaldehyde and from about 1 to 10 molar equivalents of cyclopentadiene in a solvent. The reaction is acid catalyzed, therefore, in the absence of an acid solvent, a protonated salt of the aminomethyl compound of formula II is used. The formaldehyde used may be any of the common forms available, such as: 37% aqueous formaldehyde (formalin); a solution of 55% formaldehyde, 35% methanol and 10% water (methyl formcel); or solid paraformaldehyde. Solvents which may be used should allow at least some of the protonated form of II to be in solution. Typical solvents are water or mixtures of water and a miscible organic solvent. Surprisingly, a C$_1$-C$_4$ carboxylic acid preferably glacial acetic acid may also be used. The reaction proceeds at a convenient rate at 25° C.–30° C. except when solid paraformaldehyde is used, then the formation of I depends on the rate of depolymerization of paraformaldehyde. Said rate of depolymerization is increased by decreasing the particle size of the paraformaldehyde used or heating the paraformaldehyde with acid before the addition of an aminomethyl compound of formula II such as glycine.

Other dienes that may be used in the above-described process are cyclohexadiene, butadiene or substituted cyclopentadienes, substituted cyclohexadienes and substituted butadienes such as isoprene. The substituents on the above-mentioned dienes may be lower alkyl, aryl and NO$_2$.

Using the above-said dienes, N-substituted cyclohexene compounds of formula V

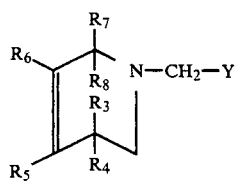

wherein R$_3$, R$_4$, R$_5$, R$_6$, R$_7$ and R$_8$ are each independently hydrogen, C$_1$-C$_4$ alkyl, C$_6$H$_5$ or NO$_2$; R$_3$ and R$_8$ may be taken together to represent [C(R$_9$)$_2$]$_n$
wherein n is 0, 1 or 2 and R$_9$ is hydrogen, C$_1$-C$_4$ alkyl, C$_6$H$_5$ or NO$_2$; Y is COOR, CON(R$_1$)$_2$ or CN wherein R, R$_1$ are each independently hydrogen or C$_1$-C$_4$ alkyl may be prepared by reacting an aminomethyl compound of formula II

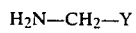
H$_2$N—CH$_2$—Y    II wherein Y is as described hereinabove for formula V with 0.9 to 10.0 molar equivalents of formaldehyde and 1.0 to 10.0 molar equivalents of a diene of formula VI

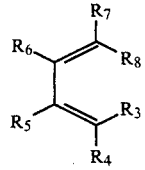

wherein R$_3$, R$_4$, R$_5$, R$_6$, R$_7$ and R$_8$ are as described hereinabove for formula V, in the presence of a solvent, preferably glacial acetic acid, at a temperature range of from 15° C. to 200° C. for a period of 1 to 24 hours.

It is an important feature of the process of the invention that the presence of water in the N-substituted azabicycloalkene or N-substituted azacycloalkene intermediate be minimized. Water reacts with compounds of formula III thus requiring the use of greater excesses of III to achieve equivalent yields. The presence of water in the reaction of an N-substituted azabicycloalkene or N-substituted azacycloalkene with compounds of formula IV result in the formation of undesirable side products. When Y is COOR and R is C$_1$-C$_4$ alkyl in formula I, the N-carboalkoxymethylazacyclohexene can be extracted into organic solvents and water can be conveniently removed. However, when Y is COOH the resulting N-carboxymethylazacyclohexene is highly water soluble and the removal of water therefrom requires distillation. Reduced pressure distillation steps may be required when the azacyclohexene compound is N-carboxymethylazanorbornene, since said compound decomposes at a significant rate above 40° C. Utilization of acetic acid as the preferred solvent when Y is COOH, and either paraformaldehyde or methyl formcel as the preferred form of formaldehyde, minimizes the amount of water present in the N-carboxymethylazacyclohexene intermediate. If methyl formcel is used, as much methanol as possible should be removed under reduced pressure before the next step. Since water is a product of the reaction shown in Flow Diagram I, approximately 1 mole of water per mole of N-substituted azacyclohexene is typically present in the product acetic acid solution.

2-Azabicyclo[2.2.1]-hept-5-ene-2-acetic acid is a zwitterionic compound at neutral pH. Said compound may be obtained as a solid by the removal of water, dissolution in ethanol and the removal of ethanol to give a solid residue which after washing with acetone, gives a white hygroscopic solid which decomposes gradually from 90° C.–135° C. Neutral and acidic solutions of 2-azabicyclo[2.2.1]-hept-5-ene-2-acetic acid are unstable due to the propensity of the compound to undergo the retro Diels-Alder reaction. Said solutions should be stored at temperatures below 40° C. The decomposition rate is such that about 25% decomposition occurs over one month at 40° C.

Other N-substituted azabicycloalkene compounds which may be prepared by the method of the invention as described hereinabove are:
2-azabicyclo[2.2.1]hept-5-ene-acetonitrile;
2-azabicyclo[2.2.1]hept-5-ene-2-acetamide;
N,N-dimethyl-2-azabicyclo[2.2.1]hept-5-ene-2-acetamide;
N-methyl-2-azabicyclo[2.2.1]hept-5-ene-2-acetamide;
2-azabicyclo[2.2.2]oct-5-ene-2-acetic acid;

2-azabicyclo[2.2.2]oct-5-ene-2-acetonitrile;
2-azabicyclo[2.2.2]oct-5-ene-2-acetamide;
N,N-dimethyl-2-azabicyclo[2.2.2]oct-5-ene-2-acetamide;
N-methyl-2-azabicyclo[2.2.2]oct-5-ene-2-acetamide;
4,5,7-trimethyl-2-azabicyclo[2.2.1]hept-5-ene-2-acetic acid;
7-methyl-2-azabicyclo[2.2.1]hept-5-ene-2-acetic acid;
6-methyl-2-azabicyclo[2.2.1]hept-5-ene-2-acetic acid;
5-methyl-2-azabicyclo[2.2.1]hept-5-ene-2-acetic acid;
4-methyl-2-azabicyclo[2.2.1]hept-5-ene-2-acetic acid;
3-methyl-2-azabicyclo[2.2.1]hept-5-ene-2-acetic acid;
1-methyl-2-azabicyclo[2.2.1]hept-5-ene-2-acetic acid;
1,4,5,6,7-pentamethyl-2-azabicyclo[2.2.1]hept-5-ene-2-acetic acid;
4,5,6,7-tetramethyl-2-azabicyclo[2.2.1]hept-5-ene-2acetic acid; and
1,4,5,6,7-pentamethyl-2-azabicyclo[2.2.1]hept-5-ene-2-acetonitrile.

N-substituted azabicycloalkene intermediates, such as the N-substituted azanorbornene intermediates of formula I, are reacted with from about 1.0 to 5.0 molar equivalents of a phosphorous compound of formula III or IV as shown below

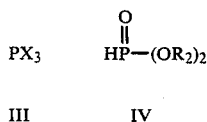

III    IV wherein X is halogen and $R_2$ is $C_1$–$C_4$ alkyl, in the presence of a solvent such as a lower alkyl alcohol or acetonitrile, or a $C_1$–$C_4$ carboxylic acid, preferably acetic acid, at a temperature such that the reaction proceeds at a convenient rate. The rate depends on the temperature at which the protonated N-substituted azabicycloalkene or N-substituted azacycloalkene intermediate undergoes the retro Diels-Alder reaction in the particular solvent that is used. A key aspect of this reaction is that the nitrogen in the intermediates of formula V be partially tetracoordinated. Typical temperatures are about 20° C.–120° C., preferably about 35° C.—80° C.; said temperatures produce a reaction time of 2 to 24 hours. If a phosphorous compound of formula IV is used, the product of the reaction is an ester which can be hydrolyzed using standard procedures such as removal of the solvent in vacuo, followed by treatment of the residue with either aqueous mineral acid or aqueous alkali base and heating to a temperature range of from about 30° C.–100° C. until hydrolysis is complete to give N-phosphonomethylglycine. If a phosphorous compound of formula III is used, the major product of the reaction is an N-acetylated compound of formula VII which is hydrolyzed by combining the reaction mixture with about 1 to 5 parts by volume of water and heating at reflux temperature. Hydrolysis is complete in about 3–6 hours at 100° C.

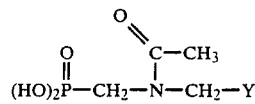

VII

If a compound of formula III is used, a sufficient amount is used to accommodate any water or alcohol present in the reaction mixture of the N-substituted azabicycloalkene or N-substituted azacycloalkene intermediate. The addition of $PX_3$ is carried out with cooling to temperatures below 30° C. Using phosphorous compounds of either formula III or IV, isolation of the product N-phosphonomethylglycine from the hydrolysis reaction is achieved by the removal of side products by filtration, concentration of the filtrate, adjustment of the pH to 1.3–1.5 to precipitate the desired product and filtration of the N-phosphonomethylglycine product.

A preferred embodiment of this invention is an integrated, single pot process wherein the N-substituted azabicycloalkene intermediate is an azanorbornene compound of formula I, preferably wherein Y is COOH, and is generated in situ by reacting glycine with from about 1.0 to 1.5 molar equivalents of formaldehyde and from about 1.0 to 2.5 molar equivalents of cyclopentadiene in the presence of glacial acetic acid at a temperature range of from about 20°–40° C., preferably 25°–35° C., for from about 1 to 24 hours; then treating this reaction mixture with from about 1.0 to 3.0 molar equivalents of a phosphorous trihalide, preferably 1.25 to 1.5 molar equivalents of phosphorous trichloride, and heating at a temperature range of from about 35°–60° C. for 5 to 16 hours; followed by combining the cooled reaction mixture with from about 1.0 to 5.0 parts by volume of water, filtering, heating at reflux to hydrolyze the N-acetyl compound of formula VII, distilling the filtrate to reduce the volume to that volume prior to combination of the reaction mixture with water, followed by cooling, filtering again and treating the filtrate with sufficient aqueous base to adjust the pH to about 1.3 to 1.5 and isolating the product N-phosphonomethylglycine by filtration. Alternatively, hydrolysis and isolation of the product N-phosphonomethylglycine may be achieved by the addition of 5 to 30 molar equivalents of water (0.1 to 1.0 parts by volume) to the cooled reaction mixture following the period of heating with phosphorous trichloride. The reaction mixture is then heated at reflux temperatures for 2 to 24 hour, cooled and filtered. The solid filtercake is recrystallized from water to give the product N-phosphonomethylglycine.

In order to facilitate a further understanding of the invention, the following examples are presented primarily for the purpose of illustrating more specific details thereof. The invention is not to be limited thereby except as defined in the claims. Unless otherwise noted, all parts are by weight and all degrees are degree centigrade.

EXAMPLE 1

Preparation of 2-azabicyclo[2.2.1]hept-5-ene acetic acid in acetic acid

A stirred mixture of glycine (7.5 g, 0.10 mole) in 35 mL of acetic acid is treated with formalin, 37% (11.3 g, 0.14 mole formaldehyde) followed by cyclopentadiene (13.2 g, 0.20 mole). After stirring for 3 hours at 25° C., a clear solution is obtained. HPLC analysis indicates the solution is 25% 2-azabicyclo[2.2.1]hept-5-ene acetic acid (N-carboxymethylazanorbornene) (quantitative yield).

EXAMPLE 2

Preparation of 2-azabicyclo[2.2.1]hept-5 ene acetic acid in water

A stirred mixture of glycine (37.5 g, 0.50 mole), 165 mL water and formalin, 37% (57 g, 0.70 mole formaldehyde) is treated with cyclopentadiene (66.0 g, 1.0 mole) at 25° C.–34° C. The reaction mixture is stirred rapidly for 15 hours, then separated to give 284.4 g of a 25% aqueous solution of the titled compound by HPLC analysis (93% yield).

The water is removed in vacuo from a portion of this aqueous solution, and the residue dissolved in a small amount of ethanol followed by removal of the ethanol in vacuo to give a solid residue. This residue is washed with acetone to give the titled product as a hygroscopic, white solid which decomposes gradually over a temperature range of 90° C.–125° C. The product is identified by proton and carbon NMR spectral analyses.

EXAMPLE 3

Preparation of N-phosphonomethylglycine via an N-substituted azanorbornene intermediate and phosphorous trichloride in acetic acid A stirred mixture of N-carboxymethylazanorbornene (4.7 g, 0.030 mole) in 40 mL of acetic acid is treated with phosphorous trichloride (8.2 g, 0.060 mole) over a 10 minute period at 20° C.–25° C. The reaction mixture is heated at 35° C.–40° C. for 6 hours, cooled to 25° C. over a 16 hour period, then combined with 100 mL water. After filtration, the filtrate is heated to reflux for 6 hours then concentrated to a final volume of 40 mL by distillation. After cooling to 20° C. and filtering, the filtrate is treated with 50% NaOH to pH 1.5. This mixture is further concentrated and cooled to yield a solid precipitate. This solid is shown to be the titled product by HPLC analysis in 46% yield and 87% purity.

EXAMPLE 4

Preparation of N-phosphonomethylglycine via an N-substituted azanorbnornene intermediate and phosphorous trichloride in propionic acid A stirred mixture of N-carboxymethylazanorbornene (4.6 g, 0.030 mole) in 40 mL of propionic acid is treated with phosphorous trichloride (8.2 g, 0.060 mole) over a 10 minute period at 20° C.–25° C. The reaction mixture is heated at 45° C.–50° C. for 4 hours, followed by heating at 74° C.–80° C. for 1 hour. After evaporation of the majority of the propionic acid in vacuo, the residue is dispersed in 75 mL of water and heated at reflux for 16 hours. Cooling to 25° C. and filtration of the reaction mixture gives a filtrate which contains the titled product in 55–60% yield by HPLC analysis.

EXAMPLE 5

Preparation of N-phosphonomethylglycine via 2-azabicyclo[2.2.1]-hept-5-ene acetic acid in a single integrated process A stirred mixture of glycine (15.0 g, 0.20 mole) and methyl formcel (55% formaldehyde, 10% water and 35% methanol) (12.2 g, 0.22 mole formaldehyde) in 60 mL glacial acetic acid at 20° C. is treated with cyclopentadiene (16.5 g, 0.25 mole). The temperature is kept at 25° C.–30° C. with ice-bath cooling to control the exotherm. The reaction is stirred at 25° C.–30° C. for 3 hours, followed by 3 hours at 25° C. under 25 inches of mercury vacuum. (HPLC assay indicates approximately 91% yield of 2-azabicyclo[2.2.1]hept-5-ene-2-acetic acid.)

The stirred reaction is treated with phosphorous trichloride (34.3 g, 0.25 mole) at 25° C., heated at 40° C.–45° C. for 4 hours, cooled to 20° C.–25° C. and added to 350 mL of water with stirring. The reaction mixture is filtered and the filter cake is washed with 50 mL of water. The combined filtrates are concentrated by distillation at 100° C.–105° C. until approximately 350 mL of distillate is collected. The reaction is cooled to 20° C.–25° C., filtered and the filtrate is treated with 50% NaOH solution to pH 1.4. The resultant precipitate is filtered to give N-phosphonomethylglycine as a grey solid, wt=28.7 g, HPLC assay indicates 63% purity.

EXAMPLE 6

Preparation of N-phosphonomethylglycine via an N-carboxymethylazanorbene intermediate and dimethylphosphite A stirred mixture of a 25% aqueous solution of N-carboxymethylazanorbornene (5.9 g, 0.010 mole) and 15 mL of acetic acid is treated with dimethyl phosphite (1.65 g, 0.015 mole) and heated at 80° C. for 3 hours. The reaction mixture is cooled to 25° C. and concentrated in vacuo. The residue is dispersed in 10 mL of concentrated HCl and 4 mL water and heated at reflux for 3 hours. After filtration, the filtrate is shown to contain the titled product by HPLC and NMR analysis.

EXAMPLE 7

Preparation of ethyl 2-azabicyclo[2.2.1]hept-5-ene-2-acetate (N-carboxymethylazanorbornene)

To a stirred solution of glycine ethyl ester hydrochloride salt (27.9 g, 0.20 mole) in 80 mL water is added formalin, 37% (22.7 g, 0.28 mole formaldehyde) followed by cyclopentadiene (26 g, 0.40 mole). The two phase reaction mixture is stirred rapidly for 4 hours, then separated. The aqueous phase is extracted with methylene chloride, then treated with 50% sodium hydroxide, with cooling to maintain a temperature of 20° C.–25° C., to pH 12. The aqueous mixture is extracted with methylene chloride and this organic phase is concentrated in vacuo to give ethyl 2-azabicyclo-[2.2.1]hept-5-ene-2-acetate as an oil, 30.0 g, 83% yield. The product is identified by proton and $^{13}C$ NMR.

EXAMPLE 8

Preparation of N-phosphonomethylglycine via an N-carboethoxymethylazanorbornene intermediate and phosphorous trichloride in acetic acid A stirred mixture of N-carboethoxymethylazanorbornene (9.05 g, 0.050 mole) in 25 mL of acetic acid is treated with phosphorous trichloride, (10.3 g, 0.075 mole) at 15° C.–20° C. and then heated at 37° C.–43° C. for 6 hours. After cooling to 25° C., the reaction mixture is added dropwise to 100 mL of water to give a slurry. The solid is removed by filtration, and the filtrate is concentrated to about 50 mL by distillation at 100° C. during which time the N-acetyl compound is hydrolyzed. The mixture is cooled to 25° C. and filtered. The pH of the filtrate is adjusted to 1.4 with 50% NaOH and is cooled to 10° C. The precipitate that forms is filtered to give 6.0 g of N-phosphonomethylglycine, 66% yield, 93% purity by HPLC.

EXAMPLE 9

Preparation of N-phosphonomethylglycine via an N-carboethoxyazanorbornene intermediate and dimethylphosphite A stirred solution of ethyl azanorbornene-N-acetate (1.8 g, 0.010 mole) in 10 mL of acetonitrile is treated with dimethylphosphite (2.2 g, 0.020 mole) and heated at reflux temperatures for 2 hours. The reaction is cooled to room temperature and concentrated in vacuo. The residue is dispersed in 10 mL of 3N HCl and heated at reflux temperatures for approximately 8 hours. HPLC analysis indicates a 50% yield of N-phosphonomethylglycine.

EXAMPLE 10

Preparation of N-phosphonomethylglycine via an N-carboethoxymethylazanorbornene intermediate and 1.0 equivalent of diethylphosphite A stirred solution of ethyl azanorbornene-N-acetate (1.8 g, 0.010 mole) in 10 mL of acetonitrile is treated with diethylphosphite (1.4 g, 0.010 mole) and heated at reflux for 2 hours. The reaction is cooled to room temperature and concentrated in vacuo. The residue is dispersed in 15 mL of 3.4N NaOH solution and heated at reflux temperatures for 3 hours, then cooled to 30° C., treated with concentrated HCl to pH 1.5, and filtered. Analysis of the filtrate by HPLC indicates a 40% yield of N-phosphonomethylglycine.

EXAMPLE 11

Preparation of N-phosphonomethylglycine via N-carboethoxymethylazanorbornene and 2.0 equivalents of diethylphosphite A stirred solution of ethyl azanorbornene-N-acetate (1.8 g, 0.010 mole) in 10 mL of ethanol is treated with diethyl phosphite (2.7 g, 0.20 mole) and heated at reflux temperatures for 2 hours. The reaction mixture is cooled to 25° C. and concentrated in vacuo. The residue is dispersed in concentrated HCl and heated to reflux temperatures until hydrolysis is complete by HPLC analysis. The reaction mixture is cooled to 25° C. and treated with 50% NaOH solution to pH 1.5 and filtered. The filtrate is concentrated in vacuo and the residue is slurried in water and filtered to give the titled product in 40% yield as a solid, identified by HPLC and NMR analysis.

I claim:

1. A method for the preparation of N-phosphonomethylglycine which comprises reacting glycine with formaldehyde and cyclopentadiene in the presence of an acid at a temperature of about 25° C. to 40° C. to yield a reaction mixture, adding phosphorous trichloride to said reaction mixture at a temperature of about 15° C. to 25° C., heating the resulting cooled reaction mixture to a temperature of about 30° C. to 80° C. to yield a heated reaction mixture, mixing the heated reaction mixture with water, filtering and hydrolyzing to obtain the N-phosphonomethylglycine.

2. A method according to claim 1 wherein the glycine is reacted with about 0.9 to 10.0 molar equivalents of formaldehyde and about 1.0 to 10.0 molar equivalents of cyclopentadiene in the presence of acetic acid.

3. A method according to claim 2 wherein about 1.0 to 5.0 molar equivalents of phosphorous trichloride are added to said reaction mixture.

4. A method according to claim 3 wherein the formaldehyde is paraformaldehyde.

5. A method according to claim 2 wherein the formaldehyde is a solution of 55% formaldehyde, 35% methanol and 10% water.

* * * * *